United States Patent [19]

Jasionowski

[11] 4,150,128

[45] Apr. 17, 1979

[54] METHOD OF TREATING ATROPHIC VULVAR DYSTROPHY

[76] Inventor: Edward A. Jasionowski, 5 Tannehill La., Parlin, N.J. 08859

[21] Appl. No.: 845,221

[22] Filed: Oct. 25, 1977

Related U.S. Application Data

[63] Continuation of Ser. No. 666,930, Mar. 15, 1976, abandoned.

[51] Int. Cl.² ................... A61K 31/56; A61K 61/63
[52] U.S. Cl. ............................... 424/240; 424/228; 424/242
[58] Field of Search ................ 424/242, 238, 240

[56] References Cited

U.S. PATENT DOCUMENTS

| | | | |
|---|---|---|---|
| 2,829,085 | 4/1958 | Gerber et al. | 424/238 |
| 3,197,367 | 7/1965 | Panzarella | 424/238 |
| 3,956,347 | 5/1976 | Laurent et al. | 424/238 X |

FOREIGN PATENT DOCUMENTS 850889  10/1960  United Kingdom ............. 424/238

*Primary Examiner*—Frederick E. Waddell
*Attorney, Agent, or Firm*—Darby & Darby

[57] ABSTRACT

The method of treating vulvar dystrophy by topically administering a progestin to the afflicted area. The preferred pharmaceutical formulation for use in the treatment consists of a hydrophilic base containing a suspension of progesterone in oil.

7 Claims, No Drawings

METHOD OF TREATING ATROPHIC VULVAR DYSTROPHY

This application is a continuation of copending application Ser. No. 666,930 filed Mar. 15, 1976 (now abandoned).

This invention pertains to the treatment of vulvar dystrophy. More particularly, the invention is related to the treatment of chronic vulvar dystrophies with progestin compounds.

As used herein the term "vulvar dystrophies" includes several related disorders afflicting the skin in the area of the vulva which have, in the past, been known as leukoplakia, leukoplakic vulvitis, lichen sclerosis et atrophicus, kraurosis vulvae, primary vulvar atrophy, sclerotic dermatoses, atrophic and hypertrophic vulvitis, and lichen simplex chronicus (localized neurodermatitis) of the vulva. The aforementioned vulvar dystrophic lesions may be segregated into three separate classifications:

The first category includes hyperplastic dystrophies which are generally characterized by a thickening of the epithelial layers and hyperkeratosis. These lesions frequently involve the hood of the clitoris, the labia majora, the interlabial sulci and may extend onto the lateral surface of the labia majora and even the adjacent thighs. Lichen simplex chronicus (neurodermatitis) and leukoplakia are usually classified as hyperplastic dystrophies.

A second category of vulvar disorders are the atrophic dystrophies, or those conditions associated with shrinkage or contracture of the vulvar skin which may also include a sclerosing progressive atrophy of the mucocutaneous teguments of the vulva leading gradually to stenosis of the vaginal orifice. The atrophic dystrophies include lichen sclerosus et atrophicus, kraurosis vulvae and atrophic vulvitis.

A third classification, mixed dystrophy, refers to those conditions in which an atrophic affliction is associated with a hyperplastic change. For example, lichen sclerosus et atrophicus is often associated with both hyperplastic epithelium and atrophic vulvar changes. This condition also includes areas of hyperplasia which develop adjacent to an otherwise atrophic lesion and which may therefore represent a form of neurodermatitis, in contrast to hyperplastic nodes mixed with the atrophic areas within the lesion per se. Microscopic evaluation of biopsied vulvar lesions has verified the coexistence of both hyperplastic and atrophic changes.

All of the preceding conditions are extensively discussed in the prior art, although it is generally acknowledged that none has a specific known cause or remedy, and because their macroscopic and microscopic appearances are so variable and interchangeable, their precise diagnosis by clinical or histological techniques is extremely difficult. While the vulvar dystrophies in themselves are responsible for a considerable degree of patient discomfort, usually being accompanied by pruritis and scaling, of greater importance is recent evidence that the associated lesions may ultimately become malignant conditions, if untreated.

Treatment of vulvar dystrophies has become largely confined to the control of symptoms, primarily pruritus. In this respect, local application of corticosteroids has been sed with some degree of success to alleviate pruritus and swelling. However, control of pruritus and burning does not assure that the lesions will regress.

More recently, investigators have found that topical application of testosterone has been successful in controlling the symptoms associated with lichen sclerosus et atrophicus. However, testosterone has been of little value for either controlling symptoms or altering the gross and histopathologic changes in vulvar tissues which accompany hyperplastic lesions. An important drawback to the use of testosterone is that it often stimulates libido, hirsutism, and causes enlargement of the clitoris.

A different treatment involves oral administration of chloroquine to treat lichen sclerosus et atrophicus. However, as this drug may induce corneal and retinal changes, it is seldom utilized.

Other investigators have advocated the use of high dosages of vitamin A and dilute hydrochloric acids to treat vulvar dystrophies. Although this treatment has occasionally provided symptomatic remission and regression of vulvar lesions, the results are unpredictable.

Finally, surgical treatment ranging from wide excision of a localized lesion to vulvectomy is utilized for those patients with uncontrollable disease. However, the high recurrence rate of the lesions associated with vulvar dystrophy requires regular observation of the patient for an extended period after surgery.

It has now been unexpectedly discovered that vulvar dystrophies may be treated successfully by topical application of a progestin, preferably progesterone, to the afflicted area. This discovery is particularly surprising in view of the limited utility of the androgen hormones in treating vulvar dystrophies. In a particularly preferred aspect of the present invention, a pharmaceutical formulation comprising a pharmaceutically acceptable hydrophilic ointment base containing a suspension of progesterone (Pregn-4-ene, 3, 20-dione) dissolved in vegetable oil is topically applied to an area afflicted with vulvar dystrophy.

As used herein the term "progestin" refers to the natural progestational hormones secreted by the corpus luteum and their synthetic equivalents. The progestins found to be useful in the present invention are those which are capable of producing progestational changes in the uterus and include, for example, progesterone (Pregn-4-ene, 3, 20-dione), 17 hydroxy progesterone, 17 alpha hydroxy progesterone caproate, pregnenolone, 17 hydroxy pregnenolone, medoxy progesterone, megesterol acetate, and 6-fluoro progesterone.

Progesterone, the preferred progestin for use in the present invention is a white or creamy white crystalline powder which is odorless and stable in air. Progesterone is practically insoluble in water, slightly soluble in vegetable oils and soluble in alcohol.

According to the present invention, one or a combination of progestins is topically applied to the afflicted vulvar area, preferably in the form of a vegetable oil solution carried in a hydrophilic ointment to treat vulvar dystrophies. In most instances the progestin agent (preferably progesterone) is dissolved in a co-solvent solution consisting of a small (about 2 to 20% by weight) quantity of a pharmaceutically acceptable alcohol (e.g., benzyl alcohol) and a major amount (20 to 98% by weight) of vegetable oil. Effective vegetable oils for use in the present invention include sesame oil, peanut oil, linseed oil, corn oil, olive oil, tung oil and the like.

The progestin in oil solution is then incorporated into a clinically acceptable carrier vehicle, preferably a hydrophilic salve, cream or ointment as for example those based on lanolin, petrolatum, white ointment (white wax and white petrolatum), or anhydrous lanolin. The progestin in oil solution is admixed with the hydrophilic carrier by conventional mixing techniques in a bowl or other suitable mixing receptacle. One carrier vehicle preferred for use in the present invention is a hydrophilic ointment prepared according to the following Example.

EXAMPLE I

| | |
|---|---|
| Methylparaben | 2.25 grams |
| Propylparaben | 0.15 grams |
| Sodium lauryl sulfate | 10 grams |
| Propylene glycol | 120 grams |
| Stearyl alcohol | 250 grams |
| White petrolatum | 250 grams |
| Purified water Q.S. to | 1000 grams |

The ointment is prepared by melting the stearyl alcohol and the white petrolatum on a steam bath. The melt is warmed to about 75 degrees. Thereafter the other ingredients, previously dissolved in the water and warmed to 75 degrees are added. The mixture is stirred until it congeals.

A commercially available hydrophilic carrier suitable for use in the present invention is available under the trademark UNIBASE from Parke-Davis & Company.

Preferably, the progestin in oil solution is suspended in the hydrophilic carrier by simply admixing the two ingredients in an open receptacle with the use of glass stirring rod. In the preferred embodiment of the invention, an oil solution of progesterone (Pregn-4-ene, 3, 20-dione) in which each ml of solution contains 25 milligrams of progesterone, 4% benzyl alcohol, 0.5% chlorbutanol (chloral derivatives) as preservatives and sesame oil (to make one ml) is admixed with 7.5 grams of a hydrophilic ointment prepared according to Example I. After the progesterone in oil has been thoroughly admixed to form a substantially uniform suspension in the carrier vehicle, the ointment is transferred to a container which is sealed and then stored. Especially good results have been obtained using this formulation in the treatment of kraurosis vulvae and leukoplakia.

Bases suitable for use as carrier vehicles in the present invention include hydrophilic materials, e.g., white ointment (simple ointment), hydrophilic petrolatum, white petrolatum, lanolin, anhydrous lanolin and similar hydrophilic salves, creams and ointments in which progesterone can be carried for topical application to the skin.

The pharmaceutical formulations of the present invention usually contain from between about 0.1 to about 5% by weight of the total formulation of the active progestin ingredient. In most instances, from about 0.25 to about 0.75% by weight, and preferably 0.35% by weight of the total formulation of a progestin, preferably progesterone, is employed. The effective dosage of the formulation of this invention required to treat vulvar dystrophy depends upon the severity of condition, stage and individual characteristics of the subject being treated. The exact dosage applied in each treatment is not critical since the effective amount may be administered in one or a plurality of treatments.

While the progestin is preferably applied to the afflicted area in the form of an ointment, as exemplified above, it may also be applied directly to the wound by spraying or swabbing it on the wound. Both the powder and the ointment may be applied first to an absorbent medium which is then applied to the afflicted area and held on by a bandage, adhesive tape or occlusive dressing. In a similar fashion, the active ingredient may be incorporated into tablets, capsules or suppositories for topical application to the afflicted vulvar passages.

The pharmaceutical formulations of the invention are preferably administered to the afflicted areas in the form of a viscous hydrophilic ointment, twice each day, in the morning and in the evening.

The progestins of the present invention may be applied alone or along with therapeutically effective agents such as ascorbic acid, ascorbyl palmitate, pharmaceutically acceptable zinc salts, e.g., zinc oxide, zince stearate, zinc citrate; antiseptics such as lydocaine, procaine, etc. and antibiotics such as neomycin, chloramphenicol, sulfanilamide, tetracycline and the like.

The effectiveness of the pharmaceutical formulations of this invention in treating vulvar dystrophies has been confirmed by clinical tests in humans. In order to provide a basis for comparison the pharmaceutical preparation used in all cases contained 25 milligrams of progesterone (Pregn-4-ene-3, 20-dione admixed with 7.5 grams of a relatively viscous hydrophilic ointment of the type disclosed in Example I herein. Each patient was instructed to apply the medication topically to the afflicted area twice a day (morning and evening). The following table summarizes the results of the clinical trials.

| PATIENT NO. | AGE | DIAGNOSIS | TREATMENT | RESULTS |
|---|---|---|---|---|
| 1 | 56 | Kraurosis vulvae - prior treatments with estrogenic vaginal creams and steroids ineffective and discontinued - the patient reported dyspareunia and localized burning - observed stenosis of the vaginal orifice - vulvar skin thin, dry, shiny and whitish in appearance - biopsy confirmed diagnosis of kraurosis vulvae | Progesterone hydrophilic ointment (prepared as above) applied topically to the afflicted area twice a day for 3 months | Whitish depigmentation almost completely disappeared and relief from dyspareunia and burning sensation after 2 weeks treatment. Discontinuance of the ointment led to a recurrence of the disease both subjectively and objectively. Re-use of the ointment promptly reversed the process and even once a day application was found sufficient. As a control progesterone was omitted from the preparation for 1 month. This modification of the |

-continued

| PATIENT NO. | AGE | DIAGNOSIS | TREATMENT | RESULTS |
|---|---|---|---|---|
| | | | | formula was accompanied by a gradual reapperance of all symptons. Subsequent treatment with a progesterone in oil suspension (UNIBASE - Park-Davis - substituted for the hydrophilic ointment of Example I) was equally effective in treating the disease. |
| 2 | 54 | Biopsied early leukoplakia. | Progesterone in oil hydrophilic ointment (as in Example I) applied topicaly to the afflicted area at least once a day for 3 months. | Dyspareunia alleviated - marked decrease in whitish appearance of vulvar tissues - biopsy conformed remission and disappearance of symptoms. |
| 3 | 47 | Pathological report of vulvar biopsy confirmed presence of cystic hyperplasia and kraurosis vulvae. | Estrogen creams and cortisone employed with no response. Progesterone hydrophilic ointment (as in Example I) applied topically to the afflicted area twice a ay for 6 months. | After 1 month's treatment dyspareunia markedly decreased - whitish lesions decreased in size and intensity. Tissues appear healthier and more pliable. |
| 4 | 54 | Biopsy confirmed kraurosis vulvae. | Progesterone in oil hydrophilic ointment (as in Example I) applied topically twice a day to the afflicted area for 1 month. | Decrease in size and number of whitish lesions on the introitus. |
| 5 | 42 | Biopsy confirmed kraurosis vulvae. | Progesterone in oil hydrophilic ointment (as in Example I) applied topically to the afflicted area twice a day for 2 weeks. | Marked relief from dryness and dyspareunia. Almost complte disappearance of whitist plaques. |
| | | | | No systemic side effects were noted in any of the above cases as confirmed by laboratory blood and urine tests. |

It should be noted that the progestin treatment of the present invention does not provide a cure for vulvar dystrophies, but rather is used to secure temporary remission and palliation of the symptoms associated with such disorders. Although application of progestin may be halted during periods of remission, treatment can be reinstituted upon recurrence or development of a new outbreak of vulvar dystrophy to provide a subsequent remission period.

What is claimed is:

1. A method of treating atrophic vulvar dystrophy in a patient afflicted with an atrophic vulvar dystrophy characterized by contracture of the vulvar skin which comprises topically applying to the afflicted area at least once a day an effective amount for treating said vulvar dystrophy of a pharmaceutical formulation consisting essentially of a pharmaceutically acceptable hydrophilic carrier containing from about 0.1% to about 5% by weight of progesterone dissolved in oil, and continuing said daily application until the symptoms accompanying said vulvar dystrophy have been alleviated.

2. The method of claim 1 wherein said vulvar dystrophy is kraurosis vulvae.

3. The method of claim 1 wherein said vulvar dystrophy is lichen sclerosis.

4. The method of claim 1 wherein said progesterone is dissolved in a vegetable oil and said vegetable oil is dispersed in said carrier.

5. The method of claim 4 wherein said pharmaceutically acceptable carrier comprises stearyl alcohol, containing a suspension of white petrolatum and propylene glycol.

6. The method of claim 4 wherein said pharmaceutical formulation includes an antibiotic.

7. The method of claim 1 wherein said pharmaceutically acceptable carrier is petrolatum.

* * * * *